US009789202B2

(12) United States Patent
Jung et al.

(10) Patent No.: US 9,789,202 B2
(45) Date of Patent: Oct. 17, 2017

(54) METHOD FOR TREATING CANCER USING AN INTERFERON ALPHA CONJUGATE

(75) Inventors: Sung Youb Jung, Suwon-si (KR); Young Eun Woo, Daejeon (KR); Se Young Lim, Gunsan-si (KR); In Young Choi, Yongin-si (KR); Jae Ho Lee, Seoul (KR); Se Chang Kwon, Seoul (KR); Sung Hwan Moon, Suwon-si (KR); Jiawang Liu, Beijing (CN)

(73) Assignees: HANMI SCIENCE CO., LTD., Hwaseong-si (KR); BEIJING HANMI PHARMACEUTICAL CO., LTD., Beijing (CN)

( * ) Notice: Subject to any disclaimer, the term of this patent is extended or adjusted under 35 U.S.C. 154(b) by 0 days.

(21) Appl. No.: 14/342,715

(22) PCT Filed: Sep. 5, 2012

(86) PCT No.: PCT/KR2012/007113
§ 371 (c)(1),
(2), (4) Date: Mar. 4, 2014

(87) PCT Pub. No.: WO2013/036032
PCT Pub. Date: Mar. 14, 2013

(65) Prior Publication Data
US 2014/0219961 A1 Aug. 7, 2014

(30) Foreign Application Priority Data
Sep. 5, 2011 (CN) .......................... 2011 1 0269277

(51) Int. Cl.
| A61K 38/21 | (2006.01) |
|---|---|
| A61K 47/48 | (2006.01) |
| A61K 31/7068 | (2006.01) |
| A61K 9/00 | (2006.01) |

(52) U.S. Cl.
CPC ...... *A61K 47/48423* (2013.01); *A61K 9/0019* (2013.01); *A61K 31/7068* (2013.01); *A61K 38/212* (2013.01); *A61K 47/48215* (2013.01); *A61K 47/48369* (2013.01)

(58) Field of Classification Search
None
See application file for complete search history.

(56) References Cited

U.S. PATENT DOCUMENTS

| 5,503,828 A | 4/1996 | Testa et al. |
|---|---|---|
| 2006/0029573 A1 | 2/2006 | Shen et al. |
| 2006/0269553 A1* | 11/2006 | Kim ................. A61K 47/48415 424/155.1 |
| 2006/0275254 A1 | 12/2006 | Kim et al. |
| 2011/0059045 A1 | 3/2011 | Melero Bermejo et al. |
| 2013/0287734 A1* | 10/2013 | Im ...................... A61K 9/0019 424/85.7 |
| 2015/0025228 A1 | 1/2015 | Jung et al. |

FOREIGN PATENT DOCUMENTS

| CN | 1723219 A | 1/2006 |
|---|---|---|
| EP | 2186830 A1 | 5/2010 |
| EP | 2196475 A1 | 6/2010 |
| JP | 2007528346 A | 10/2007 |
| JP | 2007531513 A | 11/2007 |
| JP | 2007536211 A | 12/2007 |
| JP | 2007537992 A | 12/2007 |
| JP | 2009513707 A | 4/2009 |
| KR | 10-0360594 B1 | 10/2002 |
| RU | 2179859 C1 | 2/2002 |
| WO | 96-32478 A1 | 10/1996 |
| WO | 97-34631 A1 | 9/1997 |
| WO | 2004081053 A1 | 9/2004 |
| WO | 2004093831 A2 | 11/2004 |
| WO | 2005047334 A1 | 5/2005 |
| WO | 2005/123113 A2 | 12/2005 |
| WO | 2007053574 A2 | 5/2007 |

OTHER PUBLICATIONS

Hoffmann et al. (2008), Anticancer Research, vol. 28, pp. 1499-1508.*
Adan Rios, et al., "Treatment of Acquired Immunodeficiency Syndrome-Related Kaposi's Sarcoma With Lymphoblastoid Interferon", Journal of Clinical Oncology, Apr. 1985, pp. 506-512, vol. 3, No. 4.
F.M., Torti, et al., "Alpha-Interferon in Superficial Bladder Cancer: A Northern California Oncology Group Study", Journal of Clinical Oncology, Mar. 1988, pp. 476-483, vol. 6, No. 3.
Vugrin D, et al., "Phase II study of human lymphoblastoid interferon in patients with advanced renal carcinoma", Cancer Treat Rep., Jul.-Aug. 1985, pp. 817-820, vol. 69(7-8), Abstract only.
European Patent Office: Communication dated Apr. 28, 2015 in counterpart Application No. 12830783.2.
Fuxius et al., "Gemcitabine and interferon-alpha2b in solid tumors: a phase I study in patients with advanced or metastatic non-small cell lung, ovarian, pancreatic or renal cancer", Anti-Cancer Drugs, vol. 13, Jan. 1, 2002, pp. 899-905, XP009183782, ISSN: 0959-4973.
Russian Patent Office; Communication dated Aug. 12, 2016 in counterpart application No. 2014108725/10.

(Continued)

Primary Examiner — Christine J Saoud
Assistant Examiner — Jegatheesan Seharaseyon
(74) Attorney, Agent, or Firm — Sughrue Mion, PLLC

(57) ABSTRACT

A method for preventing or treating a cancer includes administering an anti-cancer pharmaceutical composition including an interferon alpha or a polymer conjugate thereof. The pharmaceutical composition can be co-administered with anti-cancer agents. The interferon alpha conjugate shows a longer in vivo half-life and a more excellent anti-cancer activity than the conventional interferon alpha, and in particular, its co-administration with an anti-cancer agent such as gemcitabine has synergistic inhibitory effects on cancer cell growth and proliferation so as to exhibit a remarkably excellent anti-cancer activity. Further, the anti-cancer pharmaceutical composition has excellent in vivo half-life and anti-cancer activity to greatly reduce administration frequency. Co-administration of an anti-cancer agent and the interferon alpha conjugate having excellent anti-cancer activity reduces administration dose of anti-cancer agent so as to reduce side effects of anti-cancer agent and increase treatment compliance of patient.

17 Claims, 6 Drawing Sheets

(56) References Cited

OTHER PUBLICATIONS

Japanese Patent Office; Communication dated Jun. 28, 2016 in counterpart application No. 2014-529611.
State Intellectual Property Office of the People's Republic of China; Communication dated Dec. 16, 2016, issued in counterpart Application No. 201210326549.0.

Shuichi Iwahashi et al. "Histone deacetylase inhibitor augments anti-tumor effect of gemcitabine and pegylated interferon-α on pancreatic cancer cells" Int. J. Clin. Oncol. (2011) 16:671-678.

Australian Patent Office; Communication dated Oct. 6, 2016 in counterpart application No. 2012305062.

* cited by examiner

[Fig. 1]
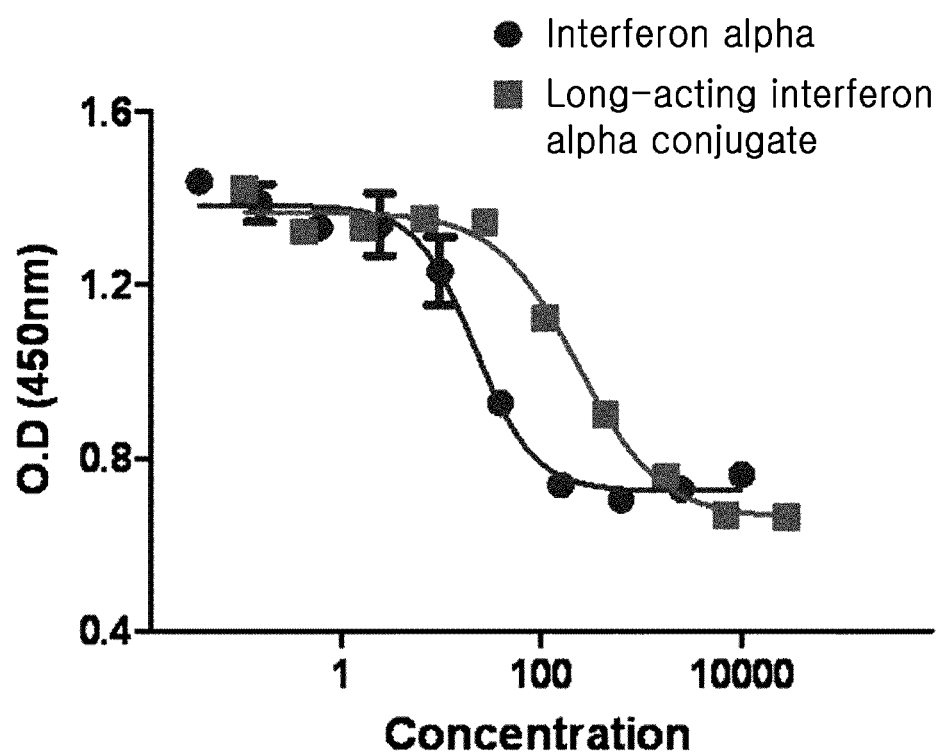

[Fig. 2]
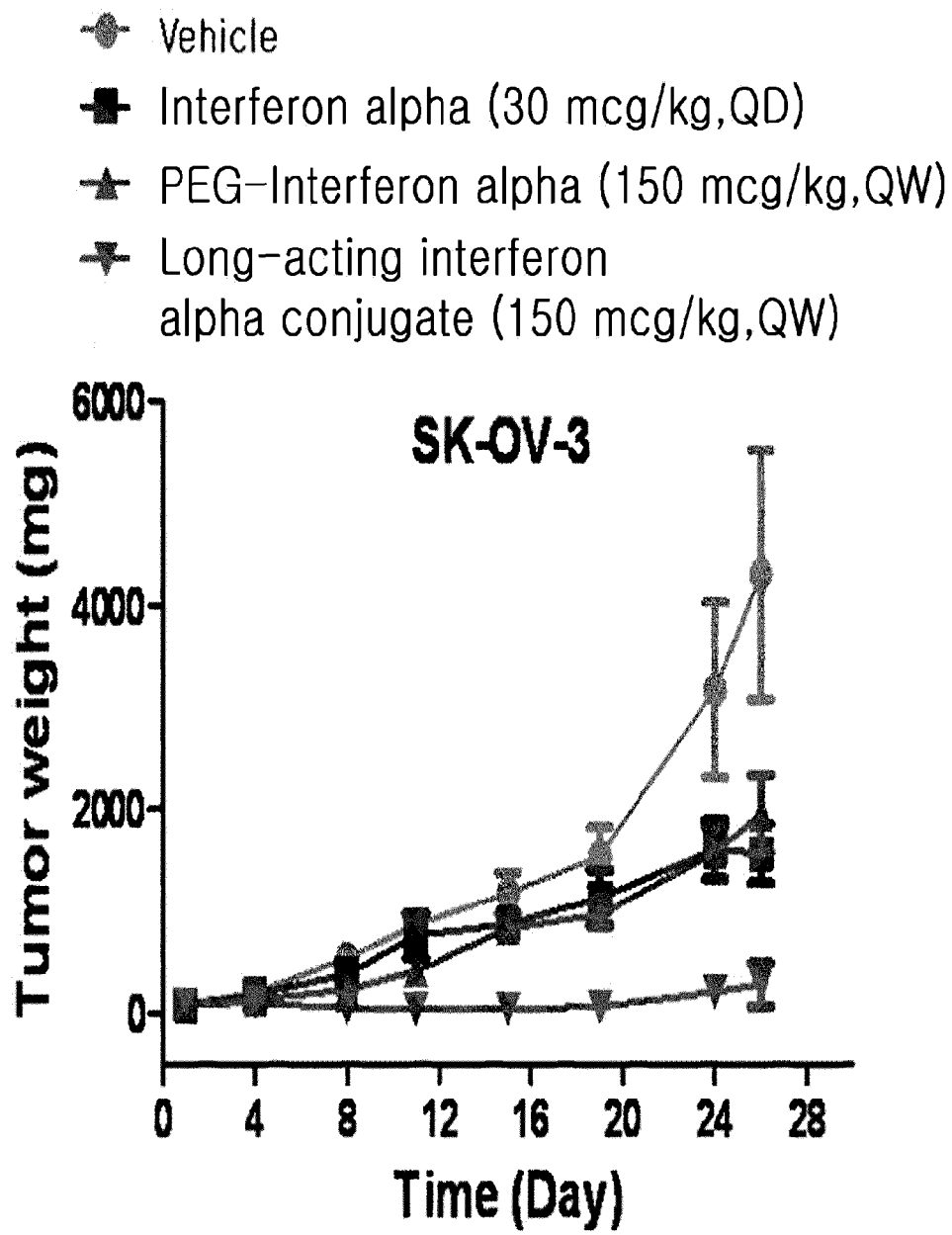

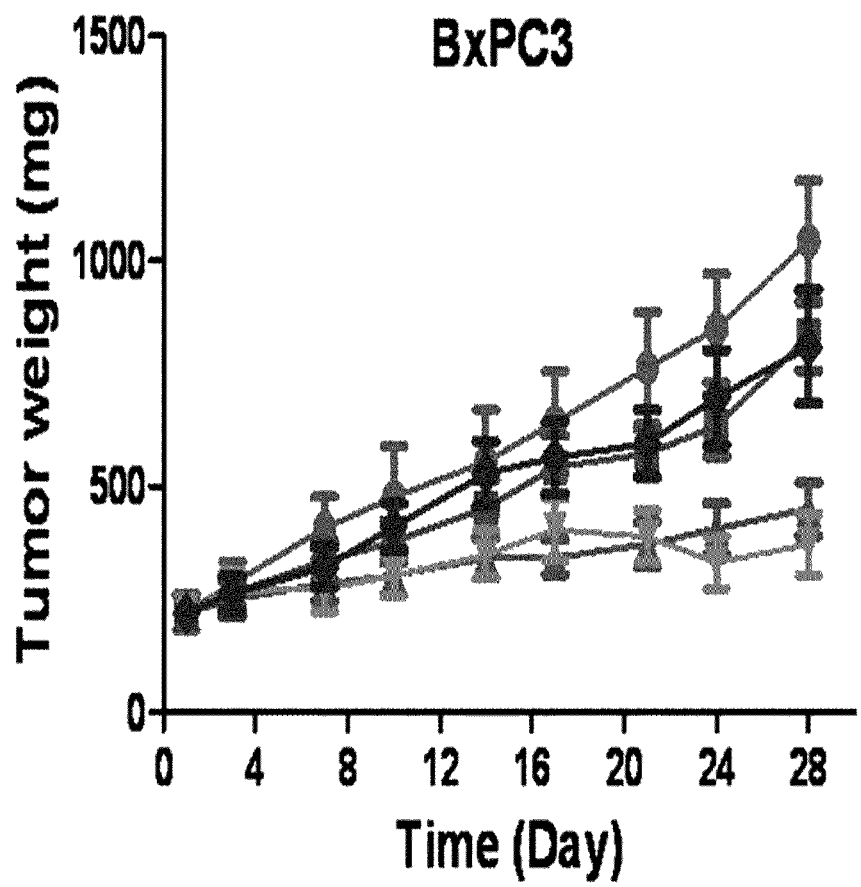
[Fig. 3]

[Fig. 4]
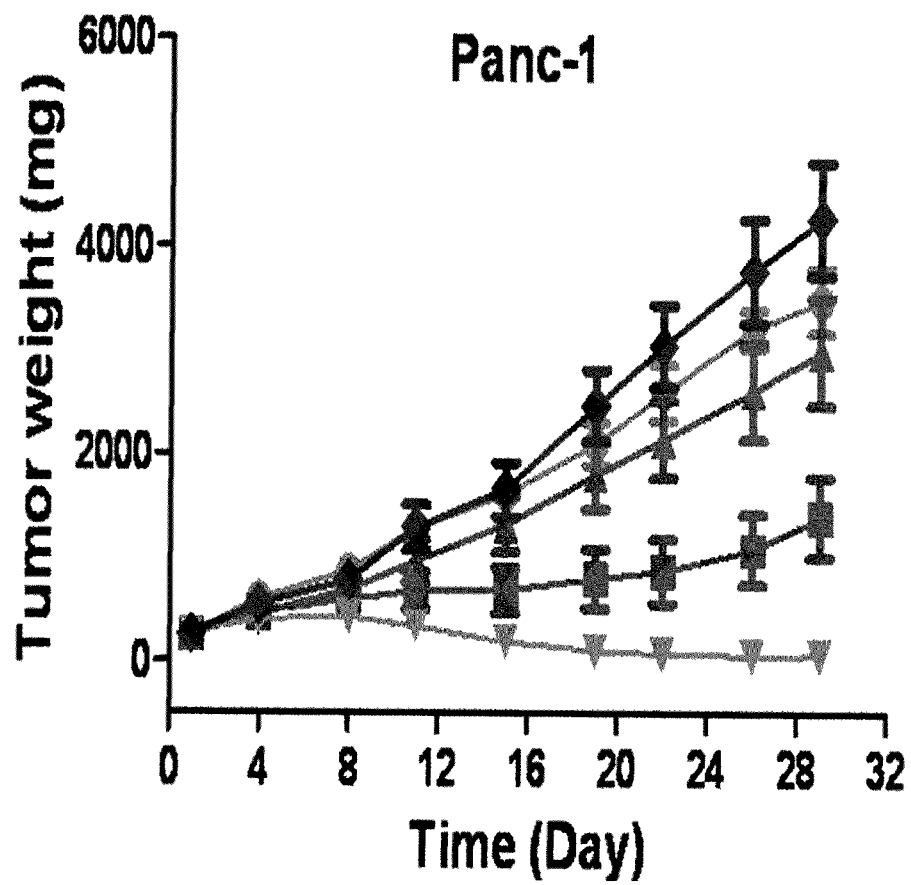

[Figure 5]

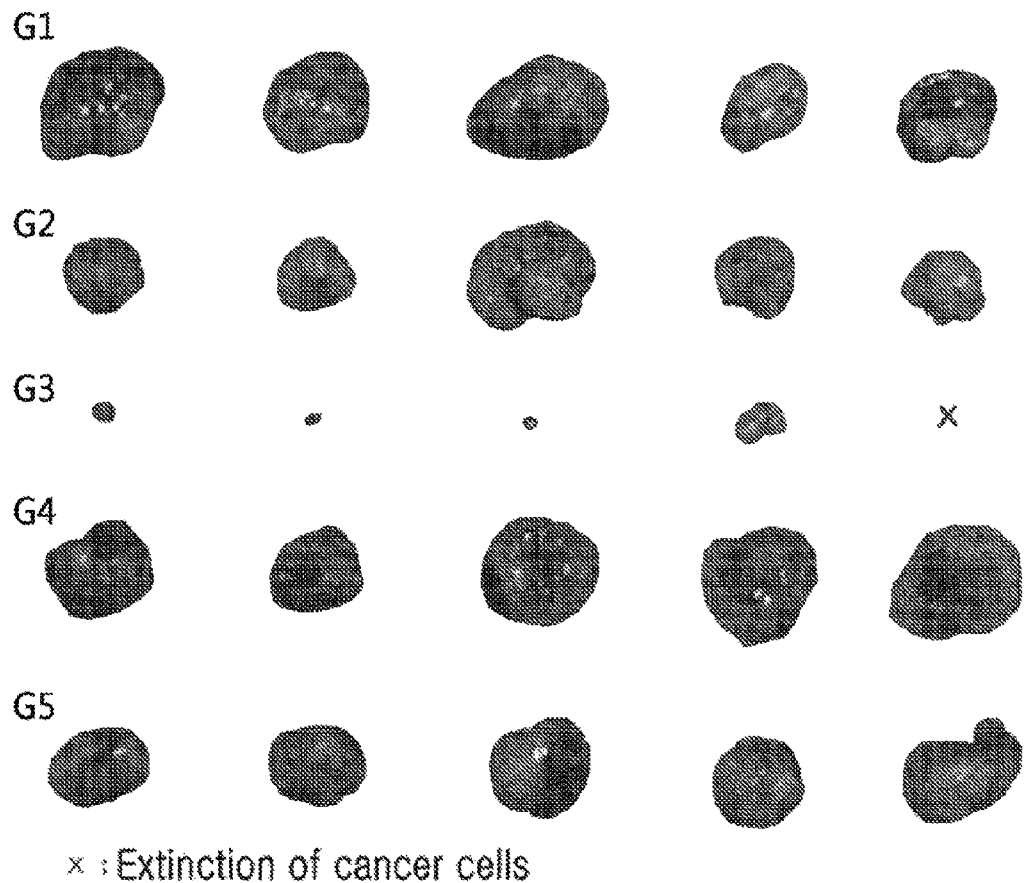

× : Extinction of cancer cells

| Group | Administered drugs |
|---|---|
| G1 | Vehicle |
| G2 | Gemcitabine (40mg/kg, Q3D, Intravenous injection) |
| G3 | Gemcitabine + Long-acting interferon alpha conjugate (40mg/kg, Q3D, Intravenous injection + 30mcg/kg, QW, Subcutaneous injection) |
| G4 | Long-acting interferon alpha conjugate (30mcg/kg, QW, Subcutaneous injection) |
| G5 | Long-acting interferon alpha conjugate (150mcg/kg, QW, Subcutaneous injection) |

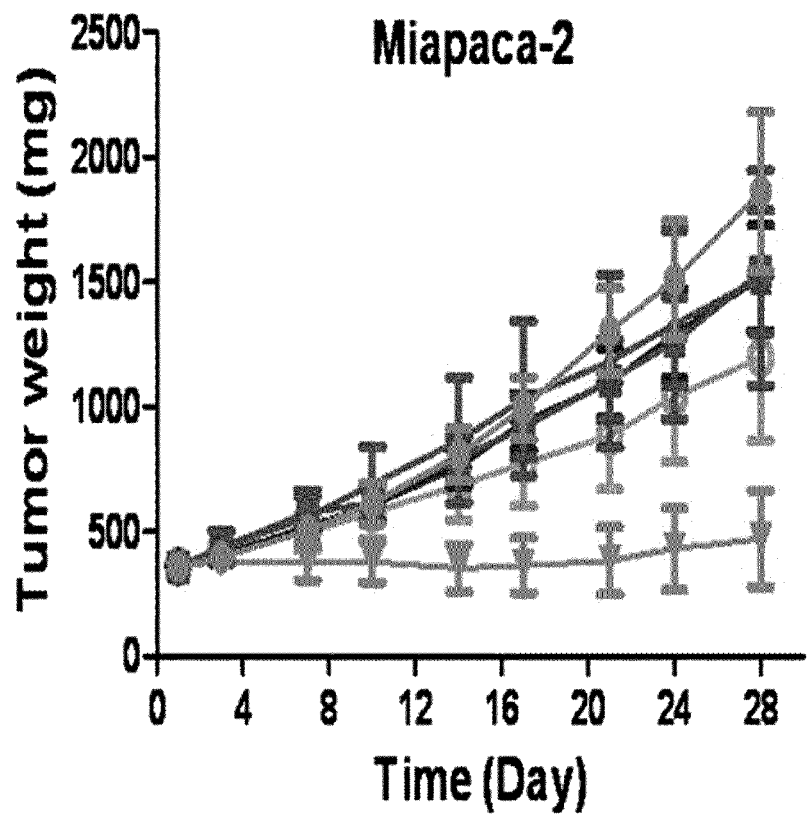
[Fig. 6]

SEQUENCE LISTING

<160> NUMBER OF SEQ ID NOS: 2

<210> SEQ ID NO 1
<211> LENGTH: 165
<212> TYPE: PRT
<213> ORGANISM: Artificial Sequence
<220> FEATURE:
<223> OTHER INFORMATION: human interferon alpha 2a

<400> SEQUENCE: 1

Cys Asp Leu Pro Glu Thr His Ser Leu Gly Ser Arg Arg Thr Leu Met

```
  1               5                  10                 15
Leu Leu Ala Gln Met Arg Lys Ile Ser Leu Phe Ser Cys Leu Lys Asp
            20                  25                 30

Arg Arg Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 2
<211> LENGTH: 165
<212> TYPE: PRT
<213> ORGANISM: Artificial Sequence
<220> FEATURE:
<223> OTHER INFORMATION: human interferon alpha 2b

<400> SEQUENCE: 2

Cys Asp Leu Pro Glu Thr His Ser Leu Gly Ser Arg Arg Thr Leu Met
 1               5                  10                 15

Leu Leu Ala Gln Met Arg Arg Ile Ser Leu Phe Ser Cys Leu Lys Asp
            20                  25                 30

Arg Arg Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165
```

METHOD FOR TREATING CANCER USING AN INTERFERON ALPHA CONJUGATE

CROSS REFERENCE TO RELATED APPLICATIONS

This application is a National Stage of International Application No. PCT/KR2012/007113, filed on Sep. 5, 2012, which claims priority from Chinese Patent Application No. 201110269277.0 filed on Sep. 5, 2011, the contents of all of which are incorporated herein by reference in their entirety.

TECHNICAL FIELD

The present invention relates to a pharmaceutical composition for preventing or treating cancer comprising an interferon alpha or conjugate thereof, and use thereof in the treatment of cancer by co-administration with anti-cancer agents.

BACKGROUND ART

Human interferon, a kind of cytokine, is a protein that inhibits proliferation of viruses, cancer cells and the like via activation of immune responses in the body and apoptosis of cancer cells. Based on the type of cell that produces the interferon, interferons are divided into three subclasses i.e., interferon alpha, interferon beta, and interferon gamma. In particular, interferon alpha is produced by B lymphocyte, null lymphocyte, and macrophage, and has antiviral and antitumor activities, activates the NK (Nature Killer) cell, and has a suppressive nature on bone marrow cells.

Recently, clinical studies have reported that recombinant human interferon alpha has therapeutic potential for the treatment of a wide variety of solid tumors, and two types of interferons prepared by recombinant DNA technology are commercially available (interferon α-2b recombinant (Intron-A, Schering Corp.); interferon α-2a recombinant (Roferon, Hoffmann-La Roche, Inc.)). Intron A is indicated for use in the treatment of malignant melanoma in combination with surgery, aggressive follicular Non-Hodgkin's Lymphoma in combination with anthracycline chemotherapy, intralesional treatment of condylomata acuminata, hairy cell leukemia, and AIDS-related Kaposi's sarcoma. Roferon is indicated for use in the treatment of Philadelphia chromosome positive chronic myelogenous leukemia (CML) and AIDS-related Kaposi's sarcoma. They are also known to be effective for bladder cancer (Torti, F. M. et al., J. clin. Onco., 3, 506-512, 1985) and renal cancer (Vugrin, D. et al., Cancer treat. Rep., 69, 817-820, 1985). Recently, interferon modified with polyethylene glycol (PEG) has been approved for use in the treatment of malignant melanoma. However, native interferon alpha or PEG-modified interferon alpha has been reported to show low anti-cancer effects because of a short half-life and low efficacy.

Cancer is an abnormal growth of cells caused by multiple changes in gene expression leading to a deregulated balance of cell proliferation and cell death, that invades and destroys nearby tissues, metastasizes to distant sites, eventually leads to death. It has been known that cancer cells abnormally divide and differentiate, arise in any tissue within the body, and are caused by a single factor or combinations thereof. These factors are environmental factors such as a wide variety of chemicals or radiation, infectious diseases such as viral infections, and hereditary factors. Cancer can be classified into several hundred types according to the organs involved and cells constituting cancer tissue.

For the treatment of cancer, surgery, radiation therapy, and chemotherapy have been used, but chemotherapy and radiation therapy have the problem of severe side effects such as vomiting and nausea, cytopenia, infection, cachexia, mucositis, hair loss, etc. In particular, the side effects of chemotherapy can dramatically affect the patient's life, and rapidly reduce the treatment compliance of patients.

Meanwhile, pancreatic cancer has a poor prognosis with a 5-year survival rate of less than 5%. Because pancreatic cancer is usually found in an advanced stage, less than 20% of patients are eligible for surgery. Despite resection, micro-metastasis and lymph nodal recurrence occur in up to 50% of patients mostly within 2 years. Pancreatic cancer is known to be one of the most lethal cancers among all gastrointestinal cancers, and it is a malignant tumor that ranks as the fourth commonest cause of cancer death in Western countries, and the sixth in Korea. Even though pancreatic cancer accounts for only 2-3% of all cancer patients, it accounts for 6% of all cancer-related deaths. Regardless of the type of chemotherapy, locally-advanced pancreatic cancer and metastatic pancreatic cancer have a median survival of 8-12 months and 3-6 months, respectively, and thus pancreatic cancer is very lethal.

A current powerful therapeutic strategy for advanced pancreatic cancer is intravenous administration of 2'-deoxy-cytidine nucleoside analogue, gemcitabine (Lilly) that is able to induce death of human pancreatic cancer cells and inhibit tumor growth and progression. However, a single administration of gemcitabine shows efficacy as low as a median overall survival of 5.7 months. Recently, erlotinib (Tarceva) in combination with gemcitabine has been approved for metastatic pancreatic cancer, and combination therapy of gemcitabine and erlotinib increased the 1-year survival rate of pancreatic cancer patients from 18% to 24%, compared to single administration of gemcitabine. However, an important factor of chemotherapy, median overall survival was increased only by 0.33 months. Erlotinib is a low molecular weight, epidermal growth factor receptor (EGFR) tyrosine kinase inhibitor, and does not distinguish cancer cells from rapidly dividing normal cells. Thus, it shows higher toxicity than a single administration of gemcitabine, and generates resistance upon long-term exposure.

For this reason, combination therapies of gemcitabine/interferon alpha, gemcitabine/cisplatin, gemcitabine/capecitabine, and gemcitabine/avastin have been attempted, in addition to the combination of gemcitabine and erlotinib. However, the therapeutic effects are not satisfactory.

DISCLOSURE

Technical Problem

Accordingly, the present inventors found that an interferon alpha conjugate prepared by linking an interferon alpha and an immunoglobulin constant region via a non-peptidyl polymer shows a longer in vivo half-life and more excellent anti-cancer activity than the conventional interferon alpha, and in particular, its co-administration with an anti-cancer agent such as gemcitabine has synergistic effects to exhibit a remarkably excellent anti-cancer activity, thereby completing the present invention. They also found that co-administration of an anti-cancer agent and the interferon alpha conjugate having excellent anti-cancer activity reduces the administration dose of anti-cancer agents so as to reduce side effects of anti-cancer agents and increase the treatment compliance of patients.

Technical Solution

An object of the present invention is to provide a pharmaceutical composition for preventing or treating cancer, comprising interferon alpha or a polymer conjugate thereof.

Another object of the present invention is to provide a pharmaceutical composition for preventing or treating cancer, comprising an interferon alpha conjugate that is prepared by linking an interferon alpha and an immunoglobulin constant region via a non-peptidyl polymer selected from the group consisting of polyethylene glycol, polypropylene glycol, a copolymer of ethylene glycol-propylene glycol, polyoxyethylated polyol, polyvinyl alcohol, polysaccharide, dextran, polyvinyl ethyl ether, polylactic acid, polylactic-glycolic acid, lipopolymers, chitins, hyaluronic acid, and a combination thereof.

Another object of the present invention is to provide a pharmaceutical composition, wherein the composition further comprises an anti-cancer agent selected from Ras inhibitor, Raf inhibitor, MEK inhibitor and MAPK inhibitor, together with the interferon alpha conjugate.

Another object of the present invention is to provide a method for treating cancer, comprising administering to a subject the pharmaceutical composition.

Advantageous Effects

An interferon alpha conjugate of the present invention shows a longer in vivo half-life and more excellent anti-cancer activity than the conventional interferon alpha, and in particular, its co-administration with an anti-cancer agent such as gemcitabine has synergistic inhibitory effects on cancer cell growth and proliferation so as to exhibits remarkably excellent anti-cancer activity. An anti-cancer pharmaceutical composition of the present invention has excellent in vivo half-life and anti-cancer activity to greatly reduce administration frequency. Co-administration of anti-cancer agents and the interferon alpha conjugate having excellent anti-cancer activity reduces the administration dose of anti-cancer agents so as to reduce side effects of anti-cancer agents and increase treatment compliance of patients.

DESCRIPTION OF DRAWINGS

FIG. 1 is a graph showing the in vitro inhibitory effects of the interferon alpha and the interferon alpha conjugate of one embodiment of the present invention on cancer cell proliferation in Daudi cells;

FIG. 2 is a graph showing changes in the tumor size after administration of interferon alpha conjugate of one embodiment of the present invention to a nude mouse (athymic BALB/c nude) subcutaneously transplanted with human ovarian cancer cells (SK-OV-3);

FIG. 3 is a graph showing changes in the tumor size after co-administration of gemcitabine and interferon alpha conjugate of one embodiment of the present invention to a nude mouse (athymic BALB/c nude) subcutaneously transplanted with human pancreatic cancer cells (BxPC-3);

FIG. 4 is a graph showing changes in the tumor size after co-administration of gemcitabine and interferon alpha conjugate of one embodiment of the present invention to a nude mouse (athymic BALB/c nude) subcutaneously transplanted with human pancreatic cancer cells (Panc-1);

FIG. 5 shows images of the tumor size examined through autopsies of individual mice after co-administration of gemcitabine and interferon alpha conjugate of one embodiment of the present invention to a nude mouse (athymic BALB/c nude) subcutaneously transplanted with human pancreatic cancer cells (Panc-1); and FIG. 6 is a graph showing changes in the tumor size after co-administration of gemcitabine and interferon alpha conjugate of one embodiment of the present invention to a nude mouse (athymic BALB/c nude) subcutaneously transplanted with human pancreatic cancer cells (Miapaca-2).

BEST MODE

In one aspect, the present invention provides a pharmaceutical composition for preventing or treating cancer, comprising interferon alpha.

The interferon alpha of the present invention, a kind of cytokine, is a protein that inhibits proliferation of viruses, cancer cells or the like via the activation of immune responses in the body and apoptosis of cancer cells. The interferon alpha is produced by B lymphocyte, null lymphocyte, and macrophage, and has antiviral and antitumor activities, activates the NK (Nature Killer) cell, and has a suppressive nature on bone marrow cells. The interferon alpha may be preferably interferon alpha 2b, interferon alpha 2a or the like.

Human interferon alpha has a molecular weight of 17,500 to 21,000, and an intrinsic activity of a very high titer of $2 \times 10^8$ IU per protein (mg). Interferon alpha in the body is a protein comprising 165 amino acids, and interferon alpha 2a (SEQ ID NO. 1) and interferon alpha 2b (SEQ ID NO. 2) have lysine and arginine at position 23, respectively.

As used herein, the interferon alpha includes a native interferon alpha, agonists, derivatives, fragments, and variants thereof, and the agonist means a substance that binds to the in vivo receptor of interferon alpha to show a biological activity identical or corresponding to that of interferon alpha, which is irrelevant to the structure of interferon alpha, and the derivative means a peptide that has at least 80% amino acid sequence homology with the native interferon alpha, which may have some groups on the amino acid residue chemically substituted, deleted, or modified, and retains the function of interferon alpha. The fragment means a peptide that has one or more amino acids added or deleted at the N-terminus or the C-terminus of the native interferon alpha, in which non-naturally occurring amino acids (for example, D-type amino acid) can be added, and retains the function of interferon alpha. The variant means a peptide that has one or more amino acid sequences different from that of the native interferon alpha, and retains the function of interferon alpha. The agonist, derivatives, fragments or variants thereof binds to in vivo receptor of interferon alpha and shows the identical or corresponding to the biological activity of the native interferon alpha.

The method for preparing the interferon alpha that can be used in the present invention is described in Korean Patent No. 10-0360594. The entire specification thereof is included in the present invention as a reference. However, the interferon alpha is not limited to that of Korean Patent No. 10-0360594 and the interferon alpha being easily prepared within the skill of the art is included in the scope of the present invention. Thus, the ordinary skill required to prepare the interferon alpha is applicable in the present invention.

Further, the present invention provides a pharmaceutical composition for preventing or treating cancer, comprising a polymer conjugate in which interferon alpha is linked to a polymer.

As used herein, the term "polymer conjugate" is the form of interferon alpha conjugated to the polymer. The polymer used in the conjugate includes all polymers which can increase in vivo half-life and therapeutic efficacy. For example, the polymer may be a polymer such as polyethylene glycol, and a protein such as an antibody, antibody fragment, fibronectin, albumin, immunoglobulin fragment or elastin, but not limited thereto.

In the polymer conjugate, the interferon alpha and the polymer may be directly linked with each other, or linked via a peptide linker or non-peptidyl linker such as non-peptidyl polymer, but not limited thereto. The protein polymer conjugate may be produced in the form of a fusion protein from a cell or cells using genetic engineering technology, or the interferon alpha and the protein polymer may be produced separately and then linked to each other ex vivo using chemical technology. The inferferon alpha conjugate in which the interferon alpha is conjugated to the polymer may be prepared by the method described in Korean Patent No. 10-0725315 and the entire specification thereof is included in the present invention as a reference. However, the preparation method of the interferon alpha conjugate is not limited thereto and includes all methods linking the polymer to the interferon alpha in order to increase the half-life of the interferon alpha. Thus, the interferon alpha conjugates being easily prepared by within the skill of the art are included in the scope of the present invention.

Further, the polymer conjugate may be a interferon alpha conjugate in which interferon alpha is linked to an immunoglobulin constant region via a non-peptidyl polymer selected from the group consisting of polyethylene glycol, polypropylene glycol, a copolymer of ethylene glycol-propylene glycol, polyoxyethylated polyol, polyvinyl alcohol, polysaccharide, dextran, polyvinyl ethyl ether, lipopolymers, chitins, hyaluronic acid, and a combination thereof. In the present invention, the polymer conjugate in which the interferon alpha is linked to the immunoglobulin constant region via the nonpeptidyl polymer may be interchangeably used with the interferon alpha conjugate.

The immunoglobulin constant region means one to four domains selected from the group consisting of $C_H1$, $C_H2$, $C_H3$ and $C_H4$ domains, which is free of heavy and light chain variable domains, or heavy chain constant domain 2 ($C_H2$) and heavy chain constant domain 3 ($C_H3$), which is free of and light chain constant domain 1 ($C_L1$) and heavy chain constant domain 1 ($C_H1$). In addition, it may further include a hinge region, and a hinge region at the heavy-chain constant region. Also, it may be a fragment having a deletion in a relatively long portion of the amino acid sequence of $C_H2$ and/or $C_H3$. Specifically, the immunoglobulin constant region of the present invention may be 1) a $C_H1$ domain, a $C_H2$ domain, a $C_H3$ domain and a $C_H4$ domain, 2) a $C_H1$ domain and a $C_H2$ domain, 3) a $C_H1$ domain and a $C_H3$ domain, 4) a $C_H2$ domain and a $C_H3$ domain, 5) a combination of one or more domains and an immunoglobulin hinge region (or a portion of the hinge region), and 6) a dimer of each domain of the heavy-chain constant regions and the light-chain constant region.

The immunoglobulin constant region of the present invention may be derived from IgG, IgA, IgD, IgE, or IgM, and each domain of the immunoglobulin constant region may be a domain hybrid of a different origin derived from an immunoglobulin selected from the group consisting of IgG, IgA, IgD, IgE and IgM. The hybrid means that sequences corresponding to two or more immunoglobulin constant regions of different origin are present in a single-chain immunoglobulin constant region. In the present invention, various types of hybrids are possible. For example, domain hybrids may be composed of one to four domains selected from the group consisting of $C_H1$, $C_H2$, $C_H3$ and $C_H4$ of IgG, IgM, IgA, IgE and IgD, and may include the hinge region.

Also, when a dimer or a multimer is formed, polypeptides encoding single-chain immunoglobulin constant regions of the same origin are linked to a single-chain polypeptide of a different origin. For example, a dimer or a multimer may be prepared by combining two or more fragments selected from the group consisting of the constant region fragments of IgG, IgA, IgM, IgD and IgE.

Preferably, it may be an immunoglobulin constant region derived from IgG or IgM, which is the most abundant protein in human blood. In the specific embodiment of the present invention, an IgG-derived immunoglobulin constant region was used. IgG can be also divided into the subclasses of IgG1, IgG2, IgG3 and IgG4, and their combinations or hybrids are permitted in the present invention. Preferably, IgG2 and IgG4 subclasses can be used, and in the specific embodiment of the present invention, an Fc domain of IgG4 free of effector functions such as complement-dependent cytotoxicity (CDC) was used.

Accordingly, an aglycosylated Fc domain of human IgG4 is the most highly preferred drug carrier. The Fc domain of human origin is advantageous over that of non-human origin because the latter may act as an antigen in the body, inducing the production of antibodies thereto.

Further, the immunoglobulin constant region may be in the form of having native sugar chains, increased sugar chains compared to a native form or decreased sugar chains compared to the native form, or may be in a deglycosylated form. The increase, decrease or removal of sugar chains of the immunoglobulin constant region may be achieved by methods commonly known in the art, such as a chemical method, an enzymatic method and a genetic engineering method using a microorganism. Herein, the removal of sugar chains from the immunoglobulin constant region results in a sharp decrease in binding affinity to the complement (c1q) and a decrease or loss in antibody-dependent cell-mediated cytotoxicity or complement-dependent cytotoxicity, thereby not inducing unnecessary immune responses in-vivo. In this regard, a deglycosylated immunoglobulin constant region prepared by the chemical or enzymatic removal of a sugar chain or an aglycosylated immunoglobulin constant region produced in prokaryotes, preferably in *E. coli*, may be more suitable to the object of the present invention as a drug carrier.

The immunoglobulin constant region of the present invention includes a native amino acid sequence, and a sequence derivative (mutant) thereof. An amino acid sequence derivative is a sequence that is different from the native amino acid sequence due to a deletion, an insertion, a non-conservative or conservative substitution or combinations thereof of one or more amino acid residues. For example, the amino acid residues at positions 214 to 238, 297 to 299, 318 to 322, or 327 to 331 of IgG Fc, which are known to play important roles in antibody binding, may be used as a suitable target for modification. Also, possible are various derivatives which lack residue forming a disulfide bond or several N-terminal amino acids of the native Fc, or have an additional methionine residue at the N terminus of the native Fc. Further, effector functions may be eliminated by removing a complement binding motif, e.g., C1q binding motif, or an ADCC (antibody-dependent cell mediated cytotoxicity) motif. Techniques of preparing such sequence derivatives of the immunoglobulin constant region are disclosed in International Patent Publication Nos. WO 97/34631 and WO 96/32478.

Amino acid exchanges in proteins and peptides, which do not generally alter the activity of molecules, are known in the art (H. Neurath, R. L. Hill, The Proteins, Academic Press, New York, 1979). Most typical substitutions occur between Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly.

If necessary, the amino acids may undergo a modification, such as phosphorylation, sulfation, acrylation, glycosylation, methylation, farnesylation, acetylation, amidation, etc.

The aforementioned constant region derivatives are derivatives that have a biological activity identical to the constant region of the present invention and improved structural stability, for example, against heat, pH, or the like.

In addition, these immunoglobulin constant regions may be obtained from human or other animals including cows, goats, swine, mice, rabbits, hamsters, rats and guinea pigs, and preferably human. The constant region of human origin is advantageous over that of non-human origin because the latter may act as an antigen in the body, inducing the production of antibodies thereto.

These Fc regions may be obtained from native forms isolated from humans and other animals including cows, goats, swine, mice, rabbits, hamsters, rats and guinea pigs, or may be recombinants or derivatives thereof, obtained from transformed animal cells or microorganisms. Herein, they may be obtained from a native immunoglobulin by isolating whole immunoglobulins from human or animal organisms and treating them with a proteolytic enzyme. For example, papain digests the native immunoglobulin into Fab and Fc regions, and pepsin treatment results in the production of pF'c and F(ab)$_2$ fragments. These fragments may be subjected, for example, to size exclusion chromatography to isolate Fc or pF'c.

In the specific embodiment of the present invention, a human IgG4-derived aglycosylated Fc region that is a recombinant immunoglobulin Fc region obtained from a microorganism was used.

The non-peptidyl polymer of the present invention means a biocompatible polymer including two or more repeating units linked to each other by any covalent bond excluding a peptide bond.

The non-peptidyl polymer which can be used in the present invention may be selected from the group consisting of polyethylene glycol, polypropylene glycol, a copolymer of ethylene glycol and propylene glycol, polyoxyethylated polyols, polyvinyl alcohol, polysaccharides, dextran, polyvinyl ethyl ether, biodegradable polymers such as PLA (polylactic acid) and PLGA (polylactic-glycolic acid), lipopolymers, chitins, hyaluronic acid, and combinations thereof, and preferably polyethylene glycol, but is not limited thereto. Also, derivatives thereof well known in the art and being easily prepared within the skill of the art are included in the scope of the present invention.

The peptide linker which is used in the fusion protein obtained by a conventional in-frame fusion method has drawbacks that it is easily cleaved in-vivo by a proteolytic enzyme, and thus a sufficient effect of increasing the blood half-life of the active drug by a carrier cannot be obtained as expected. However, in the present invention, the non-peptidyl polymer having a resistance to the proteolytic enzyme can be used to maintain the blood half-life of the active drug. Therefore, any non-peptidyl polymer can be used without any limitations, as long as it is a polymer having a resistance to the proteolytic enzyme in the body. The non-peptidyl polymer preferably has a molecular weight in the range of 1 to 100 kDa, and preferably of 1 to 20 kDa. Also, the non-peptidyl polymer of the present invention may be a single polymer or a combination of different types of polymers.

The non-peptidyl polymer used in the present invention has a reactive group capable of binding to the immunoglobulin constant region and interferon alpha at both ends. The non-peptidyl polymer has a reactive group at both ends, which may be selected from the group consisting of an aldehyde group, a propionaldehyde group, a butyraldehyde group, a maleimide group and a succinimide derivative. The succinimide derivative may be succinimidyl propionate, hydroxy succinimidyl, succinimidyl carboxymethyl, or succinimidyl carbonate.

The reactive groups at both ends of the non-peptidyl polymer may be the same or different. For example, the non-peptide polymer may possess a maleimide group at one end and at the other end, an aldehyde group, a propionaldehyde group or a butyraldehyde group.

In particular, when the non-peptidyl polymer has a reactive aldehyde group at both ends, it is effective in linking at both ends with interferon alpha and immunoglobulin constant region with minimal non-specific reactions. A final product generated by reductive alkylation by an aldehyde bond is much more stable than when linked by an amide bond. The aldehyde reactive group selectively binds to an N-terminus at a low pH, and can bind to a lysine residue to form a covalent bond at a high pH, such as pH 9.0. The interferon alpha conjugate of the present invention may be preferably a conjugate that is prepared by specifically linking the non-peptidyl polymer at the N-terminus of interferon alpha, and linking the non-peptidyl polymer at the N-terminal amine or thiol group of interferon alpha. The present inventors found that the activity of interferon alpha is increased by linking the non-peptidyl polymer at the N-terminus of interferon alpha. Preparation of the N-terminus-specific conjugate is performed by pH adjustment, and a preferred pH range is 4.5 to 7.5.

When the polyethylene glycol having a reactive hydroxy group at both ends thereof is used as the non-peptidyl polymer, the hydroxy group may be activated to various reactive groups by known chemical reactions, or a polyethylene glycol having a commercially available modified reactive group may be used.

The interferon alpha conjugate of the present invention is in the form of a conjugate prepared by linking the interferon alpha protein and the immunoglobulin constant region via the non-peptidyl polymer, and has excellent effects in maintaining in vivo persistence and stability. The immunoglobulin constant region is stable enough to be used as a carrier for a drug because it is a biodegradable polypeptide which is metabolized in vivo. In addition, owing to relatively small molecular weights, the immunoglobulin constant region has advantages over total immunoglobulin molecules in terms of the preparation, purification and yield of the conjugate. Further, because it is free of Fab that is highly different in amino acid sequence from one antibody to another, it strongly promotes the homogeneity of the conjugate and is expected to reduce the induction of antigenicity.

The interferon alpha conjugate of the present invention has increased in vivo half-life and excellent anti-cancer activity compared to the native interferon alpha. When administered, the interferon alpha conjugate of the present invention binds to the interferon alpha receptor to induce apoptosis of cancer cells, leading to a reduction in the tumor size and inhibition of tumor growth. Thus, the pharmaceutical composition comprising the interferon alpha or the conjugate thereof may be used in the prevention or treatment of cancer.

As used herein, the term "prevention" means all of the actions by which the occurrence of cancer is restrained or retarded by administration of the composition of the present invention, and the term "treatment" means all of the actions by which the symptoms of cancer have taken a turn for the better or been modified favorably by administration of the composition of the present invention.

According to one specific embodiment of the present invention, an in vitro test of anti-proliferative efficacy was performed in human Hodgkin's lymphoma cell lines, Daudi cells, and the result showed that the interferon alpha conjugate of the present invention had excellent inhibitory effects on cancer cell proliferation, compared to the native interferon alpha (Table 1, FIG. 1). According to one specific embodiment of the present invention, the interferon alpha conjugate of the present invention is administered to a nude mouse subcutaneously transplanted with human ovarian cancer cell line (SK-OV-3), and then changes in the tumor size were examined. The result showed that no changes in the tumor size was observed, compared to the negative control, native interferon alpha, and PEG-modified interferon alpha (Table 2, FIG. 2).

Further, the interferon alpha conjugate of the present invention may exhibit excellent anti-cancer activity by co-administration with an anti-cancer agent selected from Ras inhibitor, Raf inhibitor, MEK inhibitor, and MAPK inhibitor, preferably gemcitabine or sorafenib (Raf inhibitor).

The "Ras inhibitor" of the present invention refers to compounds which target, decrease or inhibit the oncogenic activity of Ras (including H-Ras, K-Ras or N-Ras), for example, farnesyl transferase inhibitor, e.g. L-744832, DK8G557 or R115777 (ZARNESTRA™).

The "Raf inhibitor" of the present invention refers to compounds which target, decrease or inhibit Raf kinase that plays an important role as an extracellular signal-regulation kinase in cell differentiation, proliferation, and apoptosis, and the target of Raf inhibitor may include, but is not limited to, RAF1. For example, it may include 3-(3,5-dibromo-4-hydroxybenzylidene)-5-iodo-1,3-dihydroindol-2-one; and benzamide, 3-(dimethylamino)-N-[3-[(4-hydroxybenzoyl)amino]-4-methylphenyl]-(9C1).

The "MEK inhibitor" of the present invention refers to compounds which target, decrease or inhibit the kinase activity of a MAP kinase kinase, MEK and the target of MEK inhibitor may include, but is not limited to, ERK and cyclin D1. Examples of the MEK inhibitor may include, but are not limited to, butanedinitrile, bis[amino[2-aminophenyl)thio]methylene]-(9C1).

The "MAPK inhibitor" of the present invention refers to compounds which target, decrease or inhibit MAP. MAP kinase (MAPK) is a group of protein serine/threonine kinases that are activated in response to a variety of extracellular stimuli and mediate signal transduction from the cell surface to the nucleus. It regulates several physiological and pathological cellular phenomena, including inflammation, apoptotic cell death, oncogenic transformation, tumor cell invasion, and metastasis. Examples of the MAPK inhibitor may include, but are not limited to, benzenesulfonamide, N-[2-[[[3-(4-chlorophenyl)-2-prophenyl]methyl]amino]methyl]phenyl]-N-(2-hydroxyethyl)-4-methoxy-(9C1).

Gemcitabine of the present invention is a compound having the general name of 2'-deoxy-2',2'-difluoro cytidine, and is a vicinol difluorine substituted deoxycytidine analogue, and may include monohydrochloride thereof and β-isomer. Gemcitabine activates RKIP (Raf kinase inhibitor Protein) and acts as the Raf inhibitor. Conventionally, gemcitabine is thought to be a drug showing the most excellent clinical activity in the treatment of pancreatic cancer. However, gemcitabine has toxicity arising from a lack of specificity between cancer cells and rapidly dividing normal cells and pre-existing or acquired resistance of most tumor cells, and thus it did not offer significant improvement in the conditions of pancreatic cancer. Combination therapies of gemcitabine/cisplatin, gemcitabine/capecitabine, gemcitabine/avastin, and gemcitabine/interferon alpha were also attempted, but the therapeutic effects were not satisfactory.

The present inventors found that co-administration of the interferon alpha conjugate of the present invention and an anti-cancer agent (overcoming k-ras mutation) selected from Ras inhibitor, Raf kinase inhibitor, MEK inhibitor, and MAPK inhibitor, in particular, gemcitabine showed a very remarkable anti-cancer activity. Activation of Ras→Raf→MEK→MAPK signal transduction pathway promotes cell differentiation and growth, and inhibits one of the interferon alpha signaling pathways, STAT to inhibit the anti-cancer activity (apoptosis) of interferon alpha. The anti-cancer agent selected from Ras inhibitor, Raf kinase inhibitor, MEK inhibitor, and MAPK inhibitor showed remarkable anti-cancer activity, when co-administered with the interferon alpha conjugate of the present invention, and in particular, it showed excellent anti-cancer activity on Panc1 and Miapaca2 pancreatic cancer cell lines with k-ras mutation, as these cells did not respond to a single administration of gemcitabine or interferon. Moreover, the remarkable anti-cancer activity was attributed to a synergistic effect, which was not observed when the anti-cancer agent was co-administered with the native interferon alpha or the PEG-modified interferon alpha. Thus, it was found that co-administration of the anti-cancer agent with the interferon alpha conjugate of the present invention induces the synergistic effect to exhibit excellent anti-cancer activity.

According to one specific embodiment of the present invention, nude mice were subcutaneously transplanted with human pancreatic cancer cell (BxPC-3), and a single administration of the interferon alpha conjugate of the present invention, or a co-administration of gemcitabine and the interferon alpha conjugate of the present invention was performed, and then changes in the tumor size were examined. The result showed that the tumor size was reduced than the negative control group, compared to a single administration of gemcitabine or PEG-modified interferon alpha (Table 3, FIG. 3).

According to a specific embodiment of the present invention, nude mice were subcutaneously transplanted with human pancreatic cancer cell (Panc-1), and co-administration of gemcitabine and the interferon alpha conjugate of the present invention was performed, and then changes in the tumor size were examined. The result showed that the tumor size was reduced when compared to the negative control group, and a synergistic effect of gemcitabine and the interferon alpha conjugate of the present invention was also observed (Table 4, FIGS. 4 and 5). According to a specific embodiment of the present invention, nude mice were subcutaneously transplanted with human pancreatic cancer cell (Miapaca-2), and co-administration of gemcitabine and the interferon alpha conjugate of the present invention was performed, and then changes in the tumor size were examined. The result showed that the tumor size was reduced when compared to the negative control group, and co-administration of gemcitabine and the interferon alpha conjugate of the present invention showed a synergistic effect, compared to co-administration of gemcitabine/PEG-modified interferon alpha (Table 5, FIG. 6).

The anti-cancer pharmaceutical composition of the present invention can be used for the treatment of cancer with k-ras mutation, preferably, for the treatment of pancreatic cancer, melanoma, renal cancer or ovarian cancer, and more preferably, for the treatment of pancreatic cancer.

The anti-cancer pharmaceutical composition of the present invention may be administered via any of the common routes, as long as the interferon alpha conjugate is able to reach a desired tissue. A variety of modes of administration are contemplated, including intraperitoneally, intravenously, intramuscularly, subcutaneously, intradermally, orally, topically, intranasally, intrapulmonarily and intrarectally, but the present invention is not limited to these exemplified modes of administration. However, since proteins are digested upon oral administration, active ingredients of a composition for oral administration should be coated or formulated for protection against degradation in the stomach. Preferably, the composition may be administered in an injectable form. In addition, the pharmaceutical composition may be administered using a certain apparatus capable of transporting the active ingredients into a target cell.

The anti-cancer pharmaceutical composition comprising the interferon alpha or the conjugate thereof the present invention may further comprises a pharmaceutically acceptable carrier. For oral administration, the pharmaceutically acceptable carrier may include a binder, a lubricant, a disintegrator, an excipient, a solubilizer, a dispersing agent, a stabilizer, a suspending agent, a coloring agent, and a perfume. For injectable preparations, the pharmaceutically acceptable carrier may include a buffering agent, a preserving agent, an analgesic, a solubilizer, an isotonic agent, and a stabilizer. For preparations for topical administration, the pharmaceutically acceptable carrier may include a base, an excipient, a lubricant, and a preserving agent. The anti-cancer pharmaceutical composition of the present invention may be formulated into a variety of dosage forms in combination with the aforementioned pharmaceutically acceptable carriers. For example, for oral administration, the pharmaceutical composition may be formulated into tablets, troches, capsules, elixirs, suspensions, syrups or wafers. For injectable preparations, the pharmaceutical composition may be formulated into an ampule as a single-dose dosage form or a unit dosage form, such as a multidose container. The composition may be also formulated into solutions, suspensions, tablets, pills, capsules and long-acting preparations.

On the other hand, examples of the carrier, the excipient, and the diluent suitable for the formulations include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oils. In addition, it may further include fillers, anti-coagulating agents, lubricants, humectants, perfumes, and antiseptics.

The administration dose of the anti-cancer pharmaceutical composition of the present invention can be determined by several related factors including the types of cancer to be treated, administration routes, the patient's age, gender, weight and severity of the illness, as well as by the types of the anti-cancer agent. Since the anti-cancer pharmaceutical composition of the present invention has excellent in vivo half-life and anti-cancer activity, it can remarkably reduce the administration frequency and dose. When co-administered with the anti-cancer agent, it can reduce the administration dose of the anti-cancer agent co-administered, thereby reducing side effects of anti-cancer agent and increasing treatment compliance of the patient.

In another aspect, the present invention provides a method for treating cancer, comprising administering to a subject the anti-cancer pharmaceutical composition comprising the interferon alpha or the conjugate thereof.

Descriptions of the interferon alpha, the pharmaceutical composition and cancer are the same as above.

In detail, the therapeutic method of the present invention includes the step of administering a pharmaceutically effective amount of the pharmaceutical composition to a subject suspected of having cancer. The subject means all mammals including dog, cow, horse, rabbit, mouse, rat, chicken and human, but the mammal of the present invention is not limited to these examples. The pharmaceutical composition may be administered via parenteral, subcutaneous, intraperitoneal, intrapulmonary, and, intranasal routes. For topical treatment, it may be administered by a suitable method including intralesional injection, if necessary. The parenteral injection includes intramuscular, intravenous, intraarterial, intraperitoneal, and subcutaneous injections. A preferred formulation is an intravenous, subcutaneous, intradermal, intramuscular or dropping injectable preparation. A preferred administration dose of the pharmaceutical composition of the present invention may vary depending on the conditions and weight of a subject, severity of the illness, drug type, administration route and period, and may be readily determined by those skilled in the art.

MODE FOR INVENTION

Hereinafter, the present invention will be described in more detail with reference to Examples. However, these Examples are for illustrative purposes only, and the invention is not intended to be limited by these Examples.

Example 1. Preparation of Interferon Alpha Conjugate

The interferon alpha used in the following experiments was prepared according to the method described in Korean Patent No. 10-0360594. The interferon alpha conjugate was prepared using the prepared interferon alpha according to the method described in Korean Patent No. 10-0725315. The representative and detailed methods are described as follows.

Example 1-1. Preparation I of IFNα-PEG-Immunoglobulin Fc Fragment Conjugate

<Step 1> Preparation of Immunoglobulin Fc Fragment Using Immunoglobulin

An immunoglobulin Fc fragment was prepared as follows. 200 mg of 150-kDa immunoglobulin G (IgG) (Green Cross, Korea) dissolved in 10 mM phosphate buffer was treated with 2 mg of a proteolytic enzyme, papain (Sigma) at 37° C. for 2 hrs with gentle agitation. After the enzyme reaction, the immunoglobulin Fc fragment regenerated thus was subjected to chromatography for purification using sequentially a SUPERDEX™ column, a protein A column and a cation exchange column. In detail, the reaction solution was loaded onto a SUPERDEX™ 200 column (Pharmacia) equilibrated with 10 mM sodium phosphate buffer (PBS, pH 7.3), and the column was eluted with the same buffer at a flow rate of 1 ml/min. Unreacted immunoglobulin molecules (IgG) and F(ab')2, which had a relatively high molecular weight compared to the immunoglobulin Fc fragment, were removed using their property of being eluted earlier than the Ig Fc fragment. Fab fragments having a molecular weight similar to the Ig Fc fragment were eliminated by protein A column chromatography. The resulting fractions containing the Ig Fc fragment eluted from the SUPERDEX™200 column were loaded at a flow rate of 5 ml/min onto a protein A column (Pharmacia) equilibrated with 20 mM phosphate buffer (pH 7.0), and the column was washed with the same buffer to remove proteins unbound to the column. Then, the protein A column was eluted with 100 mM sodium citrate buffer (pH 3.0) to obtain highly pure immunoglobulin Fc fragment. The Fc fractions collected from the protein A column were finally purified using a cation exchange column (POLYCAT™, PolyLC Company), wherein this column loaded with the Fc fractions was eluted with a linear gradient of 0.15-0.4 M NaCl in 10 mM acetate buffer (pH 4.5), thus providing highly pure Fc fractions. The highly pure Fc fractions were analyzed by 12% SDS-PAGE.

<Step 2> Preparation of IFNα-PEG Complex 3.4-kDa polyethylene glycol having an aldehyde reactive group at both ends, ALD-PEG-ALD (Shearwater), was mixed with human interferon alpha-2b (hIFNα-2b, MW: 20 kDa) dissolved in 100 mM phosphate buffer in an amount of 5 mg/ml) at an IFNα: PEG molar ratio of 1:1, 1:2.5, 1:5, 1:10 and 1:20. To this mixture, a reducing agent, sodium cyanoborohydride (NaCNBH3, Sigma), was added at a final concentration of 20 mM and was allowed to react at 4° C. for 3 hrs with gentle agitation to allow PEG to link to the amino terminal end of interferon alpha. To obtain a 1:1 complex of PEG and interferon alpha, the reaction mixture was subjected to size exclusion chromatography using a SUPERDEXR™ column (Pharmacia). The IFNα-PEG complex was eluted from the column using 10 mM potassium phosphate buffer (pH 6.0) as an elution buffer, and interferon alpha not linked to PEG, unreacted PEG and dimer byproducts where PEG was linked to two interferon alpha molecules were removed. The purified IFNα-PEG complex was concentrated to 5 mg/ml. Through this experiment, the optimal reaction molar ratio for IFNα to PEG, providing the highest reactivity and generating the smallest amount of byproducts such as dimers, was found to be 1:2.5 to 1:5.

<Step 3> Preparation of IFNα-PEG-Fc Conjugate

To link the IFNα-PEG complex purified in the above step 2 to the N-terminus of an immunoglobulin Fc fragment, the immunoglobulin Fc fragment (about 53 kDa) prepared in the above step 1 was dissolved in 10 mM phosphate buffer and mixed with the IFNα-PEG complex at an IFNα-PEG complex:Fc molar ratio of 1:1, 1:2, 1:4 and 1:8. After the phosphate buffer concentration of the reaction solution was adjusted to 100 mM, a reducing agent, NaCNBH3, was added to the reaction solution at a final concentration of 20 mM and was allowed to react at 4° C. for 20 hrs with gentle agitation. Through this experiment, the optimal reaction molar ratio for IFNα-PEG complex to Fc, providing the highest reactivity and generating the fewest byproducts such as dimers, was found to be 1:2.

<Step 4> Isolation and Purification of the IFNα-PEG-Fc Conjugate

After the reaction of the above step 3, the reaction mixture was subjected to SUPERDEX size exclusion chromatography so as to eliminate unreacted substances and byproducts and purify the IFNα-PEG-Fc protein conjugate produced. After the reaction mixture was concentrated and loaded onto a SUPERDEX column, 10 mM phosphate buffer (pH 7.3) was passed through the column at a flow rate of 2.5 ml/min to remove unbound Fc and unreacted substances, followed by column elution to collect IFNα-PEG-Fc protein conjugate fractions. Since the collected IFNα-PEG-Fc protein conjugate fractions contained a small amount of impurities, unreacted Fc and interferon alpha dimers, cation exchange chromatography was carried out to remove the impurities. The IFNα-PEG-Fc protein conjugate fractions were loaded onto a PolyCAT LP column (PolyLC) equilibrated with 10 mM sodium acetate (pH 4.5), and the column was eluted with a linear gradient of 0-0.5 M NaCl in 10 mM sodium acetate buffer (pH 4.5) using 1 M NaCl. Finally, the IFNα-PEG-Fc protein conjugate was purified using an anion exchange column. The IFNα-PEG-Fc protein conjugate fractions were loaded onto a PolyWAX LP column (PolyLC) equilibrated with 10 mM Tris-HCl (pH 7.5), and the column was then eluted with a linear gradient of 0-0.3 M NaCl in 10 mM Tris-HCl (pH 7.5) using 1 M NaCl, thus isolating the IFNα-PEG-Fc protein conjugate in a highly pure form.

Example 1-2: Preparation II of IFNα-PEG-Fc Protein Conjugate

<Step 1> Preparation of Fc-PEG Complex 3.4-kDa polyethylene glycol having an aldehyde reactive group at both ends, ALD-PEG-ALD (Shearwater), was mixed with the immunoglobulin Fc fragment prepared in the step 1 of Example 1-1 at Fc:PEG molar ratios of 1:1, 1:2.5, 1:5, 1:10 and 1:20, wherein the Ig Fc fragment had been dissolved in 100 mM phosphate buffer in an amount of 15 mg/ml. To this mixture, a reducing agent, NaCNBH3 (Sigma), was added at a final concentration of 20 mM and was allowed to react at 4° C. for 3 hrs with gentle agitation. To obtain a 1:1 complex of PEG and Fc, the reaction mixture was subjected to size exclusion chromatography using a SUPERDEXκ™ column (Pharmacia). The Fc-PEG complex was eluted from the column using 10 mM potassium phosphate buffer (pH 6.0) as an elution buffer, and immunoglobulin Fc fragment not linked to PEG, unreacted PEG and dimer byproducts where PEG was linked to two immunoglobulin Fc fragment molecules were removed. The purified Fc-PEG complex was concentrated to about 15 mg/ml. Through this experiment, the optimal reaction molar ratio for Fc to PEG, providing the highest reactivity and generating the fewest byproducts such as dimers, was found to be 1:3 to 1:10.

<Step 2> Formation and Purification of Conjugate of the Fc-PEG Complex and Interferon Alpha To link the Fc-PEG complex purified in the above step 1 to the N-terminus of IFNα, the Fc-PEG complex was mixed with IFNα dissolved in 10 mM phosphate buffer at Fc-PEG complex: IFNα molar ratios of 1:1, 1:1.5, 1:3 and 1:6. After the phosphate buffer concentration of the reaction solution was adjusted to 100 mM, a reducing agent, NaCNBH₃, was added to the reaction solution at a final concentration of 20 mM and was allowed to react at 4° C. for 20 hrs with gentle agitation. After the reaction was completed, unreacted substances and byproducts were removed according to the same purification method as in the step 4 of Example 1-1, thus isolating the Fc-PEG-IFNα protein conjugate in a highly pure form.

Example 2. In Vitro Test on Anti-Proliferative Efficacy of Interferon Alpha Conjugate in Daudi Cells Daudi cells were used, and RPMI1640 supplemented with 10% FBS and 10% PS was used as a culture medium and an experimental medium. Interferon alpha and interferon alpha conjugate of the present invention were diluted 4-fold with the experimental medium for 10 concentrations in 96-well round bottom plates. Each 50 μL of the diluted experimental medium was transferred to 96-well flat bottom plates. Daudi cells were centrifuged at 1000 rpm for 5 minutes, and then washed with 50 mL of PBS in a cornical tube. The cells were centrifuged at 1000 rpm for 5 minutes, and the experimental medium was added thereto, followed by counting the number of cells. Daudi cells were diluted to a concentration of $5 \times 10^5$ cell/mL, and then 100 μL was added to each well, followed by incubation at 37° C. for 72 hours. Then, 20 μL of CCK-8 was added to each well, and after 3 hours, absorbance was measured at 450 nm.

In vitro inhibitory effects of interferon alpha and interferon alpha conjugate of the present invention (long-acting interferon alpha conjugate) on cancer cell proliferation were examined by EC50 (Table 1, FIG. 1). As a result, the interferon alpha conjugate of the present invention showed excellent inhibitory effects on cancer cell proliferation, compared to interferon alpha.

TABLE 1

| Test group | EC50 (pg/mL) |
| --- | --- |
| Interferon alpha | 21.7 |
| Long-acting interferon alpha conjugate | 229.7 |

Example 3. In Vivo Test on Anti-Cancer Effect of Single Administration of Interferon Alpha Conjugate in Mouse Transplanted with Human Ovarian Cancer Cells In order to measure the in vivo anti-cancer effect of the interferon alpha conjugate prepared in Example 1, changes in the tumor size were examined in the mice subcutaneously transplanted with human ovarian cancer cells (SK-OV-3).

5-week old Athymic BALB/c nude mice were subcutaneously injected with $1 \times 10^8/4$ mL of SK-OV-3 cells cultured in vitro, and then cultured. Thereafter, the mice were subcutaneously transplanted with solid cancer having a size of 30 mm². Then, the mice were divided into 4 groups (G1, G2, G3, G4) of five mice each according to the size of cancer subcutaneously transplanted.

Single administrations of a control group (Vehicle), interferon alpha (30 mcg/kg, Q1D×5 times×4 weeks, subcutaneous injection), PEG-modified interferon alpha (150 mcg/kg, QW×4 weeks, subcutaneous injection), and interferon alpha conjugate of the present invention (150 mcg/kg, QW×4 weeks, subcutaneous injection) to the groups were performed. After administration of the experimental substances, changes in the tumor size of each group were measured for 4 weeks, and tumor inhibition rate relative to the control group was determined (Table 2).

As a result, an increase in the tumor size was not observed in the administration group of interferon alpha conjugate, compared to the administration groups of negative control group (Vehicle), native interferon alpha and PEG-modified interferon alpha (FIG. 2).

TABLE 2

| Administration group | Dose (mcg/kg) | Tumor inhibition rate (%, relative to vehicle) |
| --- | --- | --- |
| Interferon alpha | 30(Q1D*5)*4 weeks | 63.84 |
| PEG interferon alpha | 150 X 4 weeks | 55.49 |
| Long-acting interferon alpha conjugate | 150 X 4 weeks | 93.37 |

Example 4. In Vivo Test on Anti-Cancer Effect of Single Administration of Interferon Alpha Conjugate in Mouse Transplanted with Human Pancreatic Cancer Cells In order to measure the in vivo anti-cancer effect of the interferon alpha conjugate prepared in Example 1, changes in the tumor size were examined in the mice subcutaneously transplanted with human pancreatic cancer cells (BxPC3).

5-week old Athymic BALB/c nude mice were subcutaneously injected with $1 \times 10^8/4$ mL of BxPC3 cells cultured in vitro, and then cultured. Thereafter, the mice were subcutaneously transplanted with solid cancer having a size of 30 mm². Then, the mice were divided into 5 groups (G1, G2, G3, G4, G5) of six mice each according to the size of cancer subcutaneously transplanted.

Single administrations of a control group (Vehicle), gemcitabine (30 mg/kg, Q3D, 4 weeks, intravenous injection), PEG-modified interferon alpha (30 mcg/kg, QW×4 weeks, subcutaneous injection), and interferon alpha conjugate of the present invention (30 mcg/kg, QW, 4 weeks, subcutaneous injection) and co-administration of gemcitabine (30 mg/kg, Q3D, 4 weeks, intravenous injection) and interferon alpha conjugate of the present invention (30 mcg/kg, QW, 4 weeks, subcutaneous injection) to the groups were performed. After administration of the experimental substances, changes in the tumor size of each group were measured for 4 weeks, and tumor inhibition rate relative to the control group was determined (Table 3).

As a result, a reduction in the tumor size relative to that of the negative control group (Vehicle) was observed in the administration group of interferon alpha conjugate of the present invention and the co-administration group of gemcitabine and interferon alpha conjugate of the present invention, compared to the single administration groups of gemcitabine and PEG-modified interferon alpha (FIG. 3).

TABLE 3

| Administration group | Dose | Tumor inhibition rate (%, relative to vehicle) |
| --- | --- | --- |
| Gemcitabine | 30 mg/kg, Q3D X 4 weeks | 20 |
| Long-acting interferon alpha conjugate | 30 mcg/kg, QW X 4 weeks | 57 |
| Gemcitabine + Long-acting interferon alpha conjugate | 30 mg/kg, Q3D X 4 weeks + 30 mcg/kg, QW X 4 weeks | 64 |
| PEG interferon alpha | 30 mcg/kg, QW X 4 weeks | 22 |

Example 5. In Vivo Test on Anti-Cancer Effect of Single Administration of Interferon Alpha Conjugate in Mouse Transplanted with Human Pancreatic Cancer Cells In order to measure the in vivo anti-cancer effect of the interferon alpha conjugate prepared in Example 1, changes in the tumor size were examined in the mice subcutaneously transplanted with human pancreatic cancer cells (Panc-1).

5-week old Athymic BALB/c nude mice were subcutaneously injected with $1\times10^8/4$ mL of Panc-1 cells cultured in vitro, and then cultured. Thereafter, the mice were subcutaneously transplanted with solid cancer having a size of 30 mm². Then, the mice were divided into 5 groups (G1, G2, G3, G4, G5) of six mice each according to the size of cancer subcutaneously transplanted.

Single administrations of a control group (Vehicle), gemcitabine (40 mg/kg, Q3D, 3 weeks, intravenous injection), PEG-modified interferon alpha (30 mcg/kg, QW×3 weeks, subcutaneous injection), and interferon alpha conjugate of the present invention (30 mcg/kg, QW, 3 weeks, subcutaneous injection), and co-administration of gemcitabine (40 mg/kg, Q3D, 3 weeks, intravenous injection) and interferon alpha conjugate of the present invention (30 mcg/kg, QW, 3 weeks, subcutaneous injection) to the groups were performed. After administration of the experimental substances for 3 weeks, changes in the tumor size of each group were measured for 4 weeks, and tumor inhibition rate relative to the control group was determined (Table 4).

As a result, a reduction in the tumor size relative to that of the control group (Vehicle) was observed in the co-administration group of gemcitabine and interferon alpha conjugate of the present invention, and a synergistic effect of gemcitabine and interferon alpha conjugate of the present invention was observed (FIGS. 4 and 5).

TABLE 4

| Administration group | Dose | Tumor inhibition rate (%, relative to vehicle) |
|---|---|---|
| Gemcitabine | 40 mg/kg, Q3D X 3 weeks | 60 |
| Long-acting interferon alpha conjugate | 30 mcg/kg, QW X 3 weeks | 14 |
| Gemcitabine + Long-acting interferon alpha conjugate | 40 mg/kg, Q3D X 3 weeks + 30 mcg/kg, QW X 3 weeks | 98 |
| PEG interferon alpha | 30 mcg/kg, QW X 3 weeks | −23 |

Example 6. In Vivo Test on Anti-Cancer Effect of Single Administration of Interferon Alpha Conjugate in Mouse Transplanted with Human Pancreatic Cancer Cells In order to measure the in vivo anti-cancer effect of the interferon alpha conjugate prepared in Example 1, changes in the tumor size were examined in the mice subcutaneously transplanted with human pancreatic cancer cells (Miapaca-2).

5-week old Athymic BALB/c nude mice were subcutaneously injected with $1\times10^8/4$ mL of Miapaca-2 cells cultured in vitro, and then cultured. Thereafter, the mice were subcutaneously transplanted with solid cancer having a size of 30 mm². Then, the mice were divided into 5 groups (G1, G2, G3, G4, G5) of seven mice each according to the size of cancer subcutaneously transplanted.

Single administrations of a control group (Vehicle), gemcitabine (40 mg/kg, Q3D, 3 weeks, intravenous injection), PEG-modified interferon alpha (30 mcg/kg, QW×4 weeks, subcutaneous injection), and interferon alpha conjugate of the present invention (30 mcg/kg, QW, 4 weeks, subcutaneous injection), and co-administration of gemcitabine (40 mg/kg, Q3D, 4 weeks, intravenous injection) and interferon alpha conjugate of the present invention (30 mcg/kg, QW, 4 weeks, subcutaneous injection) to the groups were performed. After administration of the experimental substances for 3 weeks, changes in the tumor size of each group were measured for 4 weeks, and tumor inhibition rate relative to the control group was determined (Table 5).

As a result, a reduction in the tumor size relative to that of the negative control group was observed in the co-administration group of gemcitabine and interferon alpha conjugate of the present invention, and a synergistic effect of gemcitabine and interferon alpha conjugate of the present invention was observed, compared to the co-administration of gemcitabine/PEG-modified interferon alpha (FIG. 6).

TABLE 5

| Administration group | Dose | Tumor inhibition rate (%, relative to vehicle) |
|---|---|---|
| Gemcitabine | 40 mg/kg, Q3D X 4 weeks | 17 |
| Long-acting interferon alpha conjugate | 30 mcg/kg, QW X 4 weeks | 19 |
| Gemcitabine + Long-acting interferon alpha conjugate | 40 mg/kg, Q3D X 4 weeks + 30 mcg/kg, QW X 4 weeks | 75 |
| PEG interferon alpha | 30 mcg/kg, QW X 4 weeks | 19 |
| Gemcitabine + PEG interferon alpha | 40 mg/kg, Q3D X 4 weeks + 30 mcg/kg, QW X 4 weeks | 36 |

The invention claimed is:

1. A method for treating a cancer, comprising administering a composition comprising an interferon alpha conjugate and gemcitabine,
    wherein the conjugate comprises an interferon alpha, an immunoglobulin G constant region, and a polyethylene glycol linker,
    wherein the interferon alpha is linked to the immunoglobulin G constant region via the polyethylene glycol linker, and
    wherein the cancer is pancreatic cancer.

2. The method according to claim 1, wherein the immunoglobulin G constant region is an immunoglobulin G Fc region.

3. The method according to claim 1, wherein the interferon alpha is interferon alpha 2a or interferon alpha 2b.

4. The method according to claim 1, wherein the polyethylene glycol linker is linked at the N-terminus of interferon alpha in the conjugate.

5. The method according to claim 1, wherein the polyethylene glycol linker is linked at the N-terminal amine or thiol group of interferon alpha in the conjugate.

6. The method according to claim 1, wherein the immunoglobulin G constant region is aglycosylated.

7. The method according to claim 1, wherein the immunoglobulin G constant region is composed of 1 to 4 domains selected from the group consisting of $C_H1$, $C_H2$, $C_H3$ and $C_H4$ domains.

8. The method according to claim 1, wherein the immunoglobulin G constant region is composed of a dimer of the light-chain constant region and the heavy-chain constant region selected from the group consisting of $C_H1$, $C_H2$, $C_H3$ and $C_H4$ domains.

9. The method according to claim 1, wherein the immunoglobulin G constant region comprises a hinge region.

10. The method according to claim 1, wherein the immunoglobulin G constant region is a dimer or a multimer composed of single-chain immunoglobulins composed of domains of immunoglobulin G.

11. The method according to claim 1, wherein the immunoglobulin G constant region is an IgG4 Fc region.

12. The method according to claim 1, wherein the immunoglobulin G constant region is a human aglycosylated IgG4 Fc region.

13. The method according to claim 1, wherein the polyethylene glycol linker has a molecular weight ranging from 1 kDa to 100 kDa.

14. The method according to claim 1, wherein the interferon alpha is interferon alpha 2b.

15. The method according to claim 1, wherein the polyethylene glycol linker has a reactive group selected from the group consisting of an aldehyde group, a propionaldehyde group, a butyraldehyde group, a maleimide group and a succinimide derivative.

16. The method according to claim 15, wherein the succinimide derivative is succinimidyl propionate, succinimidyl carboxymethyl, hydroxy succinimidyl, or succinimidyl carbonate.

17. The method according to claim 15, wherein the polyethylene glycol linker has aldehyde reactive groups at both ends.

* * * * *